US012618056B2

(12) United States Patent
Tamori et al.

(10) Patent No.: US 12,618,056 B2
(45) Date of Patent: May 5, 2026

(54) MODIFIED ENZYME AND METHOD OF PRODUCING IMIDAZOLE DIPEPTIDE USING SAME

(71) Applicant: AJINOMOTO CO., INC., Tokyo (JP)

(72) Inventors: Mizuki Tamori, Kanagawa (JP); Uno Tagami, Kanagawa (JP); Hiroyuki Nozaki, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 301 days.

(21) Appl. No.: 18/618,330

(22) Filed: Mar. 27, 2024

(65) Prior Publication Data

US 2024/0240167 A1 Jul. 18, 2024

Related U.S. Application Data

(63) Continuation of application No. PCT/JP2022/036782, filed on Sep. 30, 2022.

(30) Foreign Application Priority Data

Sep. 30, 2021 (JP) ................................ 2021-160738

(51) Int. Cl.
*C12P 21/02* (2006.01)
*C12N 9/48* (2006.01)

(52) U.S. Cl.
CPC .............. *C12N 9/485* (2013.01); *C12P 21/02* (2013.01)

(58) Field of Classification Search
CPC ................................ C12N 9/485; C12P 21/02
USPC ........................................................ 435/68.1
See application file for complete search history.

(56) References Cited

U.S. PATENT DOCUMENTS

2005/0287627 A1 12/2005 Hashimoto et al.
2011/0081678 A1 4/2011 Takeshita et al.
2018/0179511 A1 6/2018 Kino

FOREIGN PATENT DOCUMENTS

CN 107217048 A 9/2017
CN 109851658 A 6/2019
CN 113403287 A 9/2021
JP 2013-081405 A 5/2013
JP 2018-102287 A 7/2018
WO WO2009/139392 A1 11/2009

OTHER PUBLICATIONS

Extended European Search Report for European Patent App. No. 22876557.4 (Nov. 18, 2025).

(Continued)

*Primary Examiner* — Robert B Mondesi
(74) *Attorney, Agent, or Firm* — Cermak & McGowan LLP; Shelly Guest Cermak

(57) ABSTRACT

Described herein is an enzyme useful for producing a target peptide, capable of producing the target peptide without requiring ATP. More specifically, provided herein is a modified enzyme includes an amino acid sequence such as a modified amino acid sequence including a mutation of one or more of the following amino acid residues: E81, I127, I136, T139, F140, G142, W143, I147, I181, I201, Q219, T229, M244, A249, P255, E256, I260, S293, N294, Y295, and I299 in an amino acid sequence of SEQ ID NO: 1, and having the following property (a) or (b) enhanced relative to an enzyme of the amino acid sequence of SEQ ID NO: 1:

(a) imidazole dipeptide production activity; or
(b) thermal stability.

13 Claims, 1 Drawing Sheet

Specification includes a Sequence Listing.

```
MERKRIRELL PNLRFGQFPT GPKNSLTDVP GVLVSTKSVI KPADLPHHHE VNTGVTTILP   60
RKEWFKQGCY ASYFRFNGSG EMTGSHWIDE SGLLNSPVII TNSFGVGACY NGVYEYAKKH  120
HKDEKGICDW FLTPVIAETF DGWLSDIGAM AVQSSDVVEG IENASSDAVP EGCTGGGTGM  180
ITMGFKAGTG NASRVIDSVK IDSKGEKQQV KYTLAALVQS NFGGARFLTV NGVPVGRILE  240
DEAMAAKKAG PMDGPEGSII VVIATDAPLI PIQLQRLAKR ATVGVARTGG WGSNYSGDIF  300
LAFSTAHEIP RENTQNWTPS VPQPQEVLDT ESINALFEAA FEAVEEAIYN AICMATDTKG  360
PDGREVKAID LEKLKEIVTR HAY                                           383
```

(56) References Cited

OTHER PUBLICATIONS

Database Geneseq [Online], Jan. 21, 2010 (Jan. 21, 2010), "Jan. 21, 2010 (Jan. 21, 2010), Rhodotorula minuta protein with carnosine producing activity, Seq ID:7.", XP002813712, retrieved from EBI accession No. GSP: AXS87984, Database accession No. AXS87984.
Heyland, J., et al., "Simple enzymatic procedure for 1-carnosine synthesis: whole-cell biocatalysis and efficient biocatalyst recycling," Microbial Biotechnol. 2010;3(1):74-83.
International Search Report and Written Opinion for PCT Patent App. No. PCT/JP2022/036782 (Nov. 8, 2022) with English language translation of the ISR.
Horinishi, H., et al., "Purification and Characterization of Carnosine Synthetase from Mouse Olfactory Bulbs," J. Neurochem. 1978;31:909-919.
Skaper, S. D., et al., "Some Properties of a Homocarnosine-Carnosine Synthetase Isolated from Rat Brain," J. Neurochem. 1973;21:1429-1445.

```
MERKRIRELL PNLRFGQFPT GPKNSLTDVP GVLVSTKSVI KPADLPHHHE VNTGVTTILP  60
RKEWFKQGCY ASYFRFNGSG EMTGSHWIDE SGLLNSPVII TNSFGVGACY NGVYEYAKKH 120
HKDEKGICDW FLTPVIAETF DGWLSDIGAM AVQSSDVVEG IENASSDAVP EGCTGGGTGM 180
ITMGFKAGTG NASRVIDSVK IDSKGEKQQV KYTLAALVQS NFGGARFLTV NGVPVGRILE 240
DEAMAAKKAG PMDGPEGSII VVIATDAPLI PIQLQRLAKR ATVGVARTGG WGSNYSGDIF 300
LAFSTAHEIP RENTQNWTPS VPQPQEVLDT ESINALFEAA FEAVEEAIYN AICMATDTKG 360
PDGREVKAID LEKLKEIVTR HAY                                        383
```

MODIFIED ENZYME AND METHOD OF PRODUCING IMIDAZOLE DIPEPTIDE USING SAME

This application is a Continuation of, and claims priority under 35 U.S.C. § 120 to, International Application No. PCT/JP2022/036782, filed Sep. 30, 2022, and claims priority therethrough under 35 U.S.C. § 119 to Japanese Patent Application No. 2021-160738, filed Sep. 30, 2021, the entireties of which are incorporated by reference herein. Also, the Sequence Listing filed electronically herewith is hereby incorporated by reference (File name: 2024-03-27T_US-659_Seq_List.xml; File size: 33,423 bytes; Date recorded: Mar. 19, 2024).

BACKGROUND

Technical Field

The present invention relates to a modified enzyme, a method of producing an imidazole dipeptide using the same, and the like.

Background Art

Carnosine (β-alanyl histidine) is an imidazole dipeptide composed of β-alanine and histidine. Carnosine is abundantly present in muscles, brains, and hearts of mammals including humans, and has been reported to have pH-regulating effects, anti-inflammatory effects, tissue repair effects, immunomodulatory effects, antioxidant effects, anti-protein glycation effects, and the like.

As a method of producing carnosine, a method using an enzyme that catalyzes a reaction of producing β-alanyl histidine from β-alanine and histidine (β-Ala+His→β-Ala-His) is known (Non Patent Literature 1, Non Patent Literature 2, and Patent Literature 1). However, these enzymes have required ATP in the reaction.

On the other hand, Patent Literature 2 describes that some enzymes derived from multiple microorganisms can produce β-alanyl amino acids or derivatives thereof from β-alanyl esters or β-alanyl amides and amino acids or derivatives thereof without requiring ATP, and examples of such enzymes include wild-type RhDmpA3 enzymes derived from *Rhodotorula minuta.*

Patent Literature

Patent Literature 1: United States Patent Application Publication US 2005/0287627A Patent Literature 2: International Publication WO 2009/139392A

Non Patent Literature

Non Patent Literature 1: Skaper S D et al., J Neurochem. 1973 December; 21(6): 1429-45.

Non Patent Literature 2: Horinishi H et al., J Neurochem. 1978 October; 31(4): 909-19.

SUMMARY

It is an aspect of the present invention to provide an enzyme useful for producing a target peptide, capable of producing the target peptide without requiring ATP.

As a result of an extensive study, the present inventors have found that a modified enzyme of wild-type RhDmpA3 derived from *Rhodotorula minuta* exhibits properties useful for production of a target peptide. More specifically, the present inventors have found that such a modified enzyme is excellent in imidazole dipeptide production activity and/or excellent in thermal stability without requiring ATP. The prior art neither describes nor suggests such identification.

It is an aspect of the present invention to provide a modified enzyme comprising:

(A) an amino acid sequence of SEQ ID NO: 1, wherein the amino acid sequence additionally comprises a mutation of an amino acid residue selected from the group consisting of E81, I127, I136, T139, F140, G142, W143, I147, I181, I201, Q219, T229, M244, A249, P255, E256, I260, S293, N294, Y295, I299, and combinations thereof;

(B) the amino acid sequence of (A) comprising an additional mutation of substitution, deletion, insertion, and/or addition of one or more amino acid residues; or (C) an amino acid sequence having 90% or more identity to said amino acid sequence of (A) or (B); and wherein an imidazole dipeptide production activity or thermal stability is enhanced in the modified enzyme relative to an enzyme consisting of the amino acid sequence of SEQ ID NO: 1.

It is a further aspect of the present invention to provide the modified enzyme as described above, wherein the mutation of (A) is:

(1) E81D;
(2) I127V or I127L;
(3) I136V;
(4) T139S or T139A;
(5) F140A, F140Y, F140H, F140W, F140Q, F140N, or F140D;
(6) G142A;
(7) W143F or W143A;
(8) I147A;
(9) I181V;
(10) I201F;
(11) Q219A;
(12) T229A;
(13) M244L;
(14) A249F or A249L;
(15) P255A;
(16) E256A or E256D;
(17) I260A;
(18) S293F;
(19) N294H;
(20) Y295A, Y295W, or Y295V; or
(21) I299V or I299F.

It is a further aspect of the present invention to provide the modified enzyme as described above, wherein the imidazole dipeptide production activity is an activity of producing an imidazole dipeptide from an amino acid ester and an L-amino acid having an imidazole group in a side chain.

It is a further aspect of the present invention to provide the modified enzyme as described above, wherein the amino acid ester is a compound of formula (I), the L-amino acid having an imidazole group in a side chain is an L-form of a compound of formula (II), and the imidazole dipeptide is a compound of formula (III).

It is a further aspect of the present invention to provide the modified enzyme as described above, wherein the imidazole dipeptide is carnosine or anserine.

It is a further aspect of the present invention to provide a polynucleotide encoding the modified enzyme as described above.

It is a further aspect of the present invention to provide an expression vector comprising the polynucleotide as described above.

It is a further aspect of the present invention to provide a host cell comprising an expression unit containing a polynucleotide encoding the modified enzyme as described above and a promoter operably linked thereto.

It is a further aspect of the present invention to provide a method of producing an imidazole dipeptide or a salt thereof, comprising contacting an amino acid ester or a salt thereof and an L-amino acid having an imidazole group in a side chain or a salt thereof with the modified enzyme as described above to form the imidazole dipeptide or the salt thereof.

It is a further aspect of the present invention to provide the method as described above, wherein said contacting is performed using said modified enzyme.

It is a further aspect of the present invention to provide the method as described above, wherein said contacting is performed using a host cell comprising an expression unit containing a polynucleotide encoding the modified enzyme as described above and a promoter operably linked thereto.

It is a further aspect of the present invention to provide the method as described above, wherein the amino acid ester is a compound of formula (I), the L-amino acid having an imidazole group in a side chain is an L-form of a compound of formula (II), and the imidazole dipeptide is a compound of formula (III).

It is a further aspect of the present invention to provide the method as described above, wherein the imidazole dipeptide is carnosine or anserine.

The modified enzyme as described herein does not require ATP. Therefore, an enzyme reaction using the modified enzyme as described herein can be performed at low cost.

In addition, according to the modified enzyme having an excellent imidazole dipeptide production activity, an imidazole dipeptide can efficiently be produced.

Furthermore, because the modified enzyme has excellent thermal stability, it is possible to inactivate a contaminating enzyme, such as other enzymes that utilize the same substrate to produce other products or target product-degrading enzymes, in a solution that may affect a target reaction, so that the target reaction can specifically and efficiently proceed. In addition, in view of the fact that long-term storage stability, e.g., liquid stability, of an enzyme is often and simply evaluated by an accelerated test under heating (high temperature) conditions, the modified enzyme having excellent thermal stability also has excellent long-term storage stability.

BRIEF DESCRIPTION OF DRAWINGS

FIG. 1 shows an amino acid sequence of a wild-type RhDmpA3 enzyme derived from *Rhodotorula minuta* (SEQ ID NO: 1).

DETAILED DESCRIPTION OF EXEMPLARY EMBODIMENTS

Modified Enzyme

Described herein is a modified enzyme including: (A) the amino acid sequence of SEQ ID NO: 1, except further including one or more mutations of one or more of the following amino acid residues: E81, I127, I136, T139, F140, G142, W143, I147, I181, I201, Q219, T229, M244, A249, P255, E256, I260, S293, N294, Y295, and I299; (B) the amino acid sequence of (A), further including additional mutations of substitution, deletion, insertion, and addition of an amino acid residue in the amino acid sequence; or (C) an amino acid sequence having 90% or more identity to the amino acid sequence of or (B); and wherein the modified enzyme has enhanced imidazole dipeptide production activity or enhanced thermal stability relative to an enzyme of the amino acid sequence of SEQ ID NO: 1.

The amino acid residue to be mutated in the amino acid sequence (A) is one or more of the following amino acid residues: E81, I127, I136, T139, F140, G142, W143, I147, I181, I201, Q219, T229, M244, A249, P255, E256, I260, S293, N294, Y295, and I299.

In a certain embodiment, the amino acid residue to be mutated in the amino acid sequence (A) may be one or more of the following amino acid residues: I136, T139, F140, G142, W143, I147, Q219, T229, P255, E256, I260, Y295, and I299.

In another certain embodiment, the amino acid residue to be mutated in the amino acid sequence (A) may be an amino acid residue in an α-subunit and/or an amino acid residue in a β-subunit in the enzyme having the amino acid sequence of SEQ ID NO: 1. The amino acid residue in the α-subunit is present in the region of amino acid residues at positions 1 to 257 in SEQ ID NO: 1. The amino acid residue in the β-subunit is present in the region of amino acid residues at positions 258 to 383 in SEQ ID NO: 1.

In yet another certain embodiment, the amino acid residue to be mutated in the amino acid sequence (A) may be a combination of mutations of a certain defined amino acid residue and other random amino acid residues. Certain defined amino acid residues may be, for example, one or more of the following amino acid residues: E81, I127, I181, F140, I201, M244, A249, S293, N294, and Y295. F140 or Y295 are exemplary.

The number of amino acid residues to be mutated in the amino acid sequence (A) may be, for example, 1 to 20, 1 to 10, 1 to 5, 1 to 3, or 1 or 2.

The modified enzyme having the amino acid sequence (A) is not particularly limited as long as it has the enhanced properties as described herein relative to the enzyme of the amino acid sequence of SEQ ID NO: 1, but exemplary mutations include the following: E81D, I127V, I127L, I136V, T139S, T139A, F140A, F140Y, F140H, F140W, F140N, F140Q, F140D, G142A, W143F, W143A, I147A, I181V, I201F, Q219A, T229A, M244L, A249F, A249L, P255A, E256A, E256D, I260A, S293F, N294H, Y295A, Y295W, Y295V, I299V, and I299F.

In the amino acid sequence (B), one or several amino acid residues can be modified by one or more (e.g., one, two, three, or four) additional mutations such as deletion, substitution, addition, and insertion of an amino acid residue. The additional mutations of the amino acid residue may be introduced into one region in the amino acid sequence, or may be introduced into multiple different regions in the amino acid sequence. The term "one or several" refers to a number that does not greatly impair the imidazole dipeptide production activity. The number represented by the term "one or several" is, for example, 1 to 50, 1 to 40, 1 to 35, 1 to 30, 1 to 20, 1 to 10, or 1 to 5 (e.g., 1, 2, 3, 4, or 5).

The percent identity in the amino acid sequence (C) is 90% or more. The percent identity may be 91% or more, 92% or more, 93% or more, 94% or more, 95% or more, 96% or more, 97% or more, 98% or more, or 99% or more. The percent identity can be calculated by the algorithm blastp using default settings. More specifically, the percent identity can be calculated using Scoring Parameters (Matrix: BLOSUM62; Gap Costs: Existence=11 Extension=1; Compositional Adjustments: Conditional compositional score matrix adjustment) of default settings in the algorithm blastp provided in National Center for Biotechnology Information (NCBI).

The imidazole dipeptide production activity is an activity of producing an imidazole dipeptide by bonding an amino group-containing compound and a carboxyl group-containing compound, either one contains a side chain having an imidazole group, by an amide bond. The imidazole dipeptide production activity may be an activity of producing an imidazole dipeptide from an amino acid ester as the amino group-containing compound and an L-amino acid having an imidazole group in a side chain, e.g., L-histidine or a derivative thereof, as the carboxyl group-containing compound.

In a certain embodiment, the amino acid ester may be a compound represented by the following formula (I):

(I)

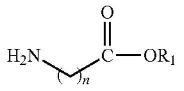

wherein $R_1$ is an alkyl group having 1 to 3 carbon atoms, and n is an integer of 1 to 4.

In a certain embodiment, the L-amino acid having an imidazole group in a side chain may be an L-form of a compound represented by the following formula (II):

(II)

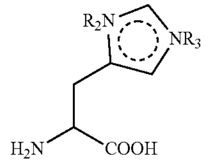

wherein $R_2$ and $R_3$ are each independently absent, a hydrogen atom, or an alkyl group having 1 to 3 carbon atoms.

In a certain embodiment, the imidazole dipeptide may be a compound represented by the following formula (III):

(III)

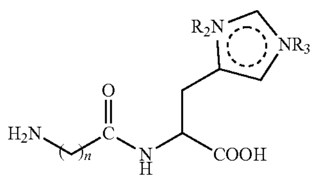

wherein $R_2$ and $R_3$ are each independently absent, a hydrogen atom, or an alkyl group having 1 to 3 carbon atoms, and n is an integer of 1 to 4.

In formulas (I) to (III), examples of the alkyl group having 1 to 3 carbon atoms include methyl, ethyl, n-propyl, and iso-propyl. The alkyl group having 1 to 3 carbon atoms is methyl or ethyl, and methyl is exemplary.

In formulas (I) and (III), n is 2 or 3, and 2 is exemplary.

In one embodiment, the imidazole dipeptide may be carnosine produced from raw materials β-alanine ester and L-histidine. In this case, the compound represented by formula (II) is an L-form of histidine represented by the following formula (II-1):

(II-1)

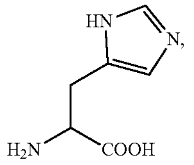

and the compound represented by formula (III) is carnosine (n=2) represented by the following formula (III-1):

(III-1)

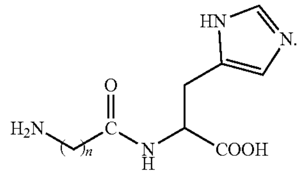

In another embodiment, the imidazole dipeptide may be a serine produced from raw materials β-alanine ester and L-3-methyl histidine. In this case, the compound represented by formula (II) is an L-form of 3-histidine represented by the following formula (II-2):

(II-2)

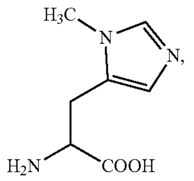

and the compound represented by formula (III) is a serine (n=2) represented by the following formula (III-2):

(III-2)

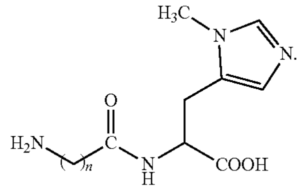

In yet another embodiment, the imidazole dipeptide may be alanine produced from raw materials β-alanine ester and L-1-methyl histidine. In this case, the compound represented by formula (II) is an L-form of 1-histidine represented by the following formula (II-3):

(II-3)

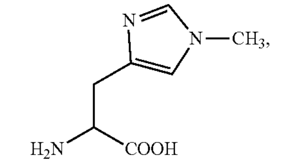

and the compound represented by formula (III) is balenine (n=2) represented by the following formula (III-3):

(III-3)

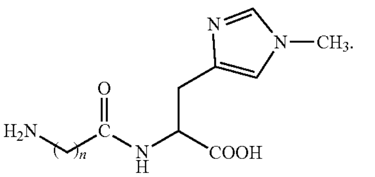

In yet another embodiment, the imidazole dipeptide may be homocarnosine produced from raw materials γ-aminobutyric acid (GABA) and L-histidine. In this case, the compound represented by formula (II) is an L-form of histidine represented by the following formula (II-1):

(II-1)

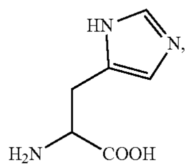

and the compound represented by formula (III) is homocarnosine (n=3) represented by the following formula (III-1):

(III-1)

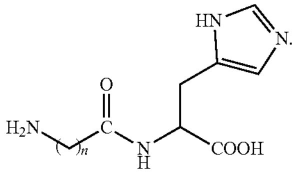

In the amino acid sequences (B) and (C), additional mutations may be introduced into sites in a catalytic domain and sites other than the catalytic domain as long as the modified enzyme can retain the imidazole dipeptide production activity. A position of an amino acid residue to which the additional mutation may be introduced is evident to a person skilled in the art. Specifically, a person skilled in the art can recognize the correlation between structure and function by (1) comparing amino acid sequences of similar multiple proteins, (2) determining relatively conserved regions and relatively not conserved regions, and then (3) predicting regions capable of playing a functionally important role and regions incapable of playing a functionally important role from the relatively conserved regions and the relatively not conserved regions, respectively. Therefore, a person skilled in the art can identify the position of the amino acid residue to which the additional mutation may be introduced in the amino acid sequence of the protein.

When the additional mutation is substitution of an amino acid residue, the substitution of the amino acid residue may be conservative substitution. As used herein, the term "conservative substitution" refers to substitution of a certain amino acid residue with an amino acid residue having a similar side chain. Families of amino acid residues having the similar side chain are well known in the art. For example, such families include amino acids having a basic side chain (e.g., lysine, arginine, histidine), amino acids having an acidic side chain (e.g., aspartic acid, glutamic acid), amino acids having an uncharged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a β position branched side chain (e.g., valine, isoleucine), amino acids having an aromatic side chain (e.g., tyrosine, phenylalanine, tryptophan, histidine), amino acids having a hydroxyl group (e.g., alcoholic, phenolic)-containing side chain (e.g., serine, threonine, tyrosine), and amino acids having a sulfur-containing side chain (e.g., cysteine, methionine). The conservative substitution of amino acids may be the substitution between aspartic acid and glutamic acid, the substitution among arginine and lysine and histidine, the substitution between tryptophan and phenylalanine, the substitution between phenylalanine and valine, the substitution among leucine and isoleucine and alanine, and the substitution between glycine and alanine.

In a certain embodiment, the modified enzyme has imidazole dipeptide production activity enhanced relative to the enzyme of the amino acid sequence of SEQ ID NO: 1. The modified enzyme may have an activity that is 1.05 times or higher, 1.10 times or higher, 1.15 times or higher, 1.20 times or higher, 1.25 times or higher, 1.30 times or higher, 1.35 times or higher, 1.40 times or higher, 1.45 times or higher, or 1.50 times or higher relative to the activity of the enzyme of the amino acid sequence of SEQ ID NO: 1.

The imidazole dipeptide production activity can be evaluated under the following measurement conditions. A purified enzyme that may be heated under conditions such as 60° C. and 2 hours is prepared, a composition of 100 mM borate buffer, 100 mM KCl, 50 mM β-alanine methyl ester (β-Ala-OMe), 100 mM histidine having an imidazole group in a side chain (L-His) or a derivative thereof (e.g., 3-methyl-L-His), an enzyme solution, and pH 8.5 is prepared, and a reaction is performed at 25° C. The reaction is stopped after 15 minutes by 50 mM $NaH_2PO_4$ (adjusted to pH 2.5 with phosphoric acid). The reaction stop solution is subjected to HPLC analysis to evaluate the imidazole dipeptide production activity.

The imidazole dipeptide production activity can be evaluated based on any one of the following:

(i) amount of dipeptide produced per unit weight of enzyme (protein);

(ii) peptide production yield relative to amino acid ester (raw material); or (iii) peptide production yield relative to amino acid having an imidazole group in a side chain (raw material).

The imidazole dipeptide production activity can be evaluated based on (i) or (ii).

In another certain embodiment, the modified enzyme has thermal stability enhanced relative to the enzyme of the amino acid sequence of SEQ ID NO: 1. The modified enzyme may have thermal stability that is 1.1 times or higher, 1.2 times or higher, 1.3 times or higher, 1.4 times or higher, 1.5 times or higher, 1.6 times or higher, 1.7 times or higher, 1.8 times or higher, 1.9 times or higher, 2.0 times or higher, 2.5 times or higher, or 3.0 times or higher relative to the thermal stability of the enzyme of the amino acid sequence of SEQ ID NO: 1.

The thermal stability of the enzyme can be evaluated by calculating the ratio of the residual activity of the enzyme solution after heating to the enzyme activity of the enzyme solution before heating (60° C., 2 hours). In such evaluation of the residual activity, the imidazole dipeptide production activity described above can be utilized.

The modified enzyme may also be a fusion protein linked to a heterologous portion through an amide bond, such as a fusion protein with a heterologous portion added at the C-terminus or N-terminus. Such a heterologous portion includes, for example, peptide components that make purification of a target protein easy, such as tag portions including a histidine tag and Strep-tag II; proteins utilized for the purification of the target protein including glutathione-S-transferase, maltose binding protein and mutants thereof, peptide components that enhance solubility of the target protein, such as a Nus-tag, peptide components that work as a chaperon, such as a trigger factor, peptide components that are recognized by a protease for cleaving the above purification tag, such as a thrombin recognition sequence or TEV protease recognition sequence, peptide components having another function, such as a full length protein or parts thereof, and linkers.

Polynucleotide

Described herein is a polynucleotide encoding the modified enzyme as described herein. The polynucleotide may be DNA or RNA, and DNA is exemplary.

The polynucleotide may be a degenerate mutant. The term "degenerate mutant" refers to a polynucleotide mutant in which at least one codon encoding a given amino acid residue before mutation has been changed to another codon encoding the same amino acid residue. Such a degenerate mutant is a silent mutation, and thus a protein (enzyme) encoded by the degenerate mutant is the same as a protein (enzyme) encoded by a polynucleotide before the mutation.

The degenerate mutant is a polynucleotide mutant in which a codon is changed to adapt to a codon usage of a host cell to which it is to be introduced. When a certain gene is expressed in a heterologous host cell, such as a microorganism, due to difference in codon usage, corresponding tRNA molecular species are sometimes not sufficiently supplied to result in a reduced translation efficiency and/or incorrect translation, such as termination of translation. For example, a low frequency of codon usage shown in Table A is known in *Escherichia coli*.

TABLE A

Low frequency codon in *Escherichia coli*

| Amino acid residue | Codon | Low frequency codon |
|---|---|---|
| Arg | AGG/AGA/CGG/CGA/CGU/CGC | AGG/AGA/CGG/CGA |
| Gly | GGG/GGA/GGU/GGC | GGA |
| Ile | AUA/AUU/AUC | AUA |
| Leu | UUG/UUA/CUG/CUA/CUU/CUC | CUA |
| Pro | CCG/CCA/CCU/CCC | CCC |

Therefore, it is possible to use a degenerate mutant that adapts to a codon usage of a host cell as described herein. For example, the degenerate mutants may be those in which a codon(s) encoding one or more of the following amino acid residues has been changed: an arginine residue, a glycine residue, an isoleucine residue, a leucine residue, and a proline residue. More specifically, the degenerate mutants that may be changed may be low frequency codon, such as AGG, AGA, CGG, CGA, GGA, AUA, CUA, and CCC. The degenerate mutant may include changes of one or more (e.g., one, two, three, four, or five) of the following codons:

i) at least one of the four codons encoding Arg (AGG, AGA, CGG, and CGA) changed to another codon that encodes Arg (CGU or CGC);
ii) one codon encoding Gly (GGA) changed to another codon encoding Gly (GGG, GGU, or GGC);
iii) one codon encoding Ile (AUA) changed to another codon encoding Ile (AUU or AUC);
(iv) one codon encoding Leu (CUA) changed to another codon encoding Leu (UUG, UUA, CUG, CUU, or CUC); and
(v) one codon encoding Pro (CCC) changed to another codon encoding Pro (CCG, CCA, or CCU).

When the degenerate mutant is RNA, a nucleotide residue "U" should be used as described above, but when the degenerate mutant is DNA, "T" should be used in place of the nucleotide residue "U". The number of mutations of nucleotide residues for adapting the codon usage in a host cell is not particularly limited as long as the nucleotide residues encode the same protein before and after the mutation, and for example is 1 to 400, 1 to 300, 1 to 200, or 1 to 100.

A low frequency codon can easily be identified based on a type of any host cell and genome sequence information by utilizing known technology in the art. Therefore, the degenerate mutant may include the change of a low frequency codon to a non-low frequency codon (e.g., high frequency codon). Methods of designing mutants by taking account of not only the low frequency codons but also factors such as compatibility to a genomic GC content of a production bacterium strain have been known (Alan Villalobos et al., Gene Designer: a synthetic biology tool for constructing artificial DNA segments, BMC Bioinformatics; 2006 Jun. 6; 7:285). Thus, such methods may be utilized. In this way, the mutants described herein can appropriately be made depending on a type of any host cell, such as the microorganism described herein, into which it can be introduced.

Expression Vector

Described herein is an expression vector. The expression vector may include a polynucleotide encoding the modified enzyme as described herein. The expression vector may include an expression unit containing a polynucleotide encoding the modified enzyme as described herein and a promoter operably linked thereto.

The term "expression unit" refers to the minimum unit including a given polynucleotide to be expressed as a protein and a promoter operably linked thereto and enabling transcription of the polynucleotide and further production of the protein encoded by the polynucleotide. The expression unit may further include elements such as a terminator, a ribosome binding site, and a drug resistant gene. The expression unit may be DNA or RNA, and DNA is exemplary. The expression unit may be homologous/native or heterologous/non-native to the host cell. The expression unit may also include one polynucleotide to be expressed as a protein and a promoter operably linked thereto, that is, an expression unit enabling expression of monocistronic mRNA, or an expression unit including a plurality of polynucleotides to be expressed as proteins, that is 2 or more, 3 or more, 4 or more, 5 or more, or 10 or more polynucleotides, and promoters operably linked thereto, that is, an expression unit enabling expression of polycistronic mRNA. The expression unit can be included in a genomic region, that is, a natural genomic region that is a natural locus in which the polynucleotide encoding the above protein inherently occurs or a non-natural genomic region that is not the natural locus, or a non-genomic region (e.g., intracellularly) in a microorganism (host cell). The expression unit may be included at one or two or more (e.g., one, two, three, four, or five) different positions in the genomic region. Specific forms of the expression unit included in the non-genomic region include, for example, plasmids, viral vectors, phages, and artificial chromosomes.

A promoter that constitutes the expression unit is not particularly limited as long as it permits expression of a protein (enzyme) encoded by a polynucleotide linked downstream thereto in the host cell. For example, the promoter may be homologous or heterologous to the host cell. For example, constitutive or inducible promoters commonly used for the production of recombinant proteins can be used. Such promoters include, for example, PhoA promoter, PhoC promoter, T7 promoter, T5 promoter, T3 promoter, lac promoter, trp promoter, trc promoter, tac promoter, PR promoter, PL promoter, SP6 promoter, arabinose inducible promoter, cold shock promoter, tetracycline inducible promoter, and rpoH promoter. A promoter having a potent transcription activity in a host cell can be used. The promoter having the potent transcription activity in the host cell includes, for example, promoters of genes highly expressed in host cells and promoters from viruses.

An expression vector may further include elements such as a terminator, a ribosome binding site, and a drug resistant gene that function in a host cell as an expression unit, in addition to the minimum unit described herein. Drug resistant genes include, for example, genes resistant to drugs such as tetracycline, ampicillin, kanamycin, hygromycin, phosphinothricin, and chloramphenicol.

An expression vector may also further include a region capable of homologous recombination with the genome of a host cell so that homologous recombination with the genomic DNA of the host cell can occur. For example, the expression vector may be designed so that an expression unit contained therein is located between a pair of homologous regions, such as homologous homology arm, loxP, FRT to a certain sequence in the genome of the host cell. A genomic region (target of a homologous region) of the host cell to which an expression unit is to be introduced is not particularly limited, and may be a locus of a gene highly expressed in amount in the host cell.

An expression vector may be a plasmid, a viral vector, a phage, or an artificial chromosome. The expression vector may be an integrative vector or a non-integrative vector. The integrative vector may be a vector that is entirely integrated into the genome of the host cell. Alternatively, the integrative vector may be a vector, only a part, such as an expression unit, of which is integrated into the genome of the host cell. The expression vector may further be a DNA vector or an RNA vector (e.g., a retrovirus vector). The expression vector may also be a commonly used expression vector. Such expression vectors include, for example, pUC (e.g., pUC19, pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30), pET (e.g., pET28a), and derivatives thereof.

Host Cell

Described herein is a host cell. The host cell as described herein includes an expression unit of a polynucleotide encoding the modified enzyme as described herein. The host cell can include an expression unit containing a polynucleotide encoding the modified enzyme and a promoter operably linked thereto. The host cell can be a microorganism.

The host cell can be a transformed microorganism. Examples of the host cell include bacteria such as bacteria belonging to Enterobacteriaceae, and fungi. The bacteria may be gram-positive bacteria or gram-negative bacteria. The gram-positive bacteria include, for example, bacteria in the genera *Bacillus* and *Corynebacterium*. *Bacillus subtilis* is an example of bacterium in the genus *Bacillus*. *Corynebacterium glutamicum* is an example of a bacterium in the genus *Corynebacterium*. The gram-negative bacteria include, for example, bacteria in the genera *Escherichia* and *Pantoea*. *Escherichia coli* is an example of a bacterium in the genus *Escherichia*. *Pantoea ananatis* is an example of a bacterium in the genus *Pantoea*. Microorganisms in the genera *Saccharomyces* and *Schizosaccharomyces* are examples of fungi. *Saccharomyces cerevisiae* is an example of a microorganism in the genus *Saccharomyces*. *Schizosaccharomyces pombe* is an example of a microorganism in the genus *Schizosaccharomyces*. The host cell can be a bacterium belonging to Enterobacteriaceae, and bacteria in the genera *Escherichia* and *Pantoea* are particular examples, and *Escherichia coli* and *Pantoea ananatis* are further particular examples.

In one embodiment, the host cell can be used to produce an imidazole dipeptide or a salt thereof by using the modified enzyme as described herein produced in the host cell, using the host cell itself (e.g., host cell cultures) or a treated product thereof, such as disrupted host cells, lysed host cells, lyophilized host cells.

In another embodiment, the host cell can be used to obtain the modified enzyme.

The host cell may be further genetically modified. Such modifications include, for example:

(1) deficiency or weakening of an amino acid-degrading enzyme;

(2) deficiency or weakening of an amino acid ester-degrading enzyme; or (3) deficiency or weakening of a peptide-degrading enzyme.

Examples of the host cell in which the enzyme of (1), (2), or (3) is weakened or defective include a host cell containing a mutation that reduces or deletes the expression level of the enzyme in the genome of the host cell, and a host cell containing a mutation that reduces or deletes the activity of the enzyme in the genome of the host cell.

The host cell can be made by any known method in the art. For example, the transformed microorganism as described above can be made by a method using an expression vector (e.g., a competent cell method, an electroporation method) or genome modification technology. When the expression vector is an integrative vector that produces homologous recombination with genomic DNA of a host cell, an expression unit can be integrated into the genomic DNA of the host cell by transformation. On the other hand, when the expression vector is a non-integrative vector that does not prompt homologous recombination with genomic DNA of a host cell, the expression unit is not integrated into the genomic DNA of the host cell by transformation, and can remain as a an expression vector, and exist independently from the genomic DNA. Alternatively, according to genome-editing technology (e.g., CRISPR/Cas System), it is possible to integrate the expression unit into the genomic DNA of the host cell and modify the native expression unit inherently possessed by the host cell.

The culture conditions for culturing the host cell as described herein is not particularly limited, and standard cell culture conditions can be chosen depending on the host. The medium for culturing the transformed microorganism is known, and for example, a nutrient medium such as an LB medium or a minimum medium such as an M9 medium can be added with the addition of a carbon source, a nitrogen source, a vitamin source, or the like.

The culture temperature is 4 to 40° C., or 10 to 37° C. The culture time is 5 to 168 hours, or 8 to 72 hours. As a gas composition, a $CO_2$ concentration is about 6% to about 84%, and a pH is about 5 to 9. Also the culture can be performed under an aerobic, anoxic, or anaerobic conditions depending on nature of a host cell.

Any appropriate methods can be used as a culture method. Depending on the host cell, either a shaking culture or static culture is possible, but stirring may be performed as necessary, or aeration may be performed. Such a culture method includes, for example, a batch culture method, a feeding culture method, and a continuous culture method. When the expression of a certain protein produced by the transformed microorganism is under the control of an inducible promoter such as lac promoter, the expression of the protein may be induced by adding an inducer such as IPTG (isopropyl-β-thiogalactopyranoside) to the culture medium.

The modified enzyme produced in the host cell as described herein can be purified from an extract of the host cell by any purification method. Examples of such a purification method include salting out, a precipitation method (e.g., isoelectric point precipitation method, solvent precipitation method), a method using a molecular weight difference (e.g., dialysis, ultrafiltration, gel filtration), chromatography (e.g., ion exchange chromatography, hydrophobic chromatography, reverse phase chromatography, affinity chromatography), electrophoresis (e.g., SDS polyacrylamide electrophoresis, isoelectric focusing), or a combination thereof. When the modified enzyme is secreted, a culture supernatant containing the modified enzyme is obtained by removing microbial cells from a culture medium obtained by culturing the modified enzyme, by centrifugation or the like. The modified enzyme can be purified from this culture supernatant.

Method of Producing Imidazole Dipeptide or Salt Thereof

A method of producing an imidazole dipeptide or a salt thereof is described herein. The method includes steps of contacting an amino acid ester or a salt thereof and an amino acid having an imidazole group in a side chain or a salt thereof with the modified enzyme to form the imidazole dipeptide or the salt thereof.

The imidazole dipeptide, the amino acid ester, and the amino acid having an imidazole group in a side chain are as described above.

Examples of the salt include inorganic salts and organic salts. Examples of the inorganic salt include a salt of a metal (e.g., monovalent metals such as lithium, sodium, potassium, rubidium, and cesium, and divalent metals such as calcium, magnesium, and zinc), a salt of an inorganic acid (e.g., hydrochloride, sulfate), and a salt of an inorganic base (e.g., ammonia). Examples of the organic salt include a salt with an organic acid (e.g., acetic acid, succinic acid, malonic acid, oxalic acid) and a salt of an organic base (e.g., ethylenediamine, propylenediamine, ethanolamine, monoalkylethanolamine, dialkylethanolamine, diethanolamine, triethanolamine).

In one embodiment, the above contacting may be performed using the modified enzyme in an aqueous solution (i.e., enzyme method). The modified enzyme may be an unpurified, crude, or purified enzyme. The modified enzyme can be utilized in the form of the host cell or a treated product thereof (e.g., disrupted microorganisms, lysed microorganisms, lyophilized microorganisms). The modified enzyme may also be utilized in a form immobilized on a solid phase.

When the method is performed using the modified enzyme in an aqueous solution, an aqueous solution containing (a) the modified enzyme, (b) an amino acid ester or a salt thereof, and (c) an amino acid having an imidazole group in a side chain or a salt thereof can be used as a reaction system. In such a case, the modified enzyme can be brought into contact with the amino acid ester or a salt thereof and the amino acid having an imidazole group in a side chain or a salt thereof in the aqueous solution to allow a target reaction to proceed. The aqueous solution can be a buffer. Examples of the buffer include a phosphate buffer, a Tris buffer, a carbonate buffer, an acetate buffer, and a citrate buffer. A pH is, for example, 6 to 10, or 7.5 to 9.5. Amounts of the modified enzyme, the amino acid ester or a salt thereof, and the amino acid having an imidazole group in a side chain or a salt thereof (substrate) in the reaction system, and a reaction time can be appropriately adjusted according to an amount of the imidazole dipeptide or a salt thereof to be produced. A reaction temperature is not particularly limited as long as the reaction proceeds, and is, for example, 5 to 40° C., 8 to 30° C.

In another embodiment, the above-mentioned contacting may be performed using the host cell in a culture medium (i.e., fermentation method). In such a case, a culture solution containing (a) the host cell, (b) an amino acid ester or a salt thereof, and (c) an amino acid having an imidazole group in a side chain or a salt thereof can be used as a reaction system. In such a case, the modified enzyme can be brought into contact with the amino acid ester or a salt thereof and the amino acid having an imidazole group in a side chain or a salt thereof in the culture solution or the host cell contained in the culture solution to allow a target reaction to proceed. In such a case, the method can be performed under the same conditions as the culture conditions of the host cell (e.g., culture solution, culture temperature). Amounts of the modified enzyme, the amino acid ester or a salt thereof, and the amino acid having an imidazole group in a side chain or a salt thereof (substrate), and a reaction time can be appropriately adjusted according to an amount of the imidazole dipeptide or a salt thereof to be produced.

The imidazole dipeptide or a salt thereof obtained by the method can be purified by any purification method. As such a purification method, for example, the same method as the above-described purification method for the modified enzyme can be used.

Subsequently, the present invention is described in detail with reference to Examples, but the present invention is not limited to the following Examples.

EXAMPLES

Example 1: Construction of Histidine-Tagged Mutant RhDmpA3 Expression Plasmid An expression unit of RhDmpA3 including a nucleotide sequence encoding an amino acid sequence of RhDmpA3 (SEQ ID NO: 1) and a nucleotide sequence encoding an rpoH promoter from an *E. coli* MG1655 strain (SEQ ID NO: 2) operably linked thereto was designed. A plasmid in which such an expression unit was inserted into XbaI and HindIII sites in a multiple cloning site of pUC18 (Takara Bio Inc.) was generated and named prpoH_01_RhDmpA(3) (purchased from GenScript Japan Inc.). For an rpoH promoter sequence from the *E. coli* MG1655 strain, reference was made to the information published on genome.jp/kegg. An amino acid sequence encoded by an RhDmpA3 gene corresponds to an amino acid sequence of amino acid residues at positions 13 to 395 in the amino acid sequence of SEQ ID NO: 5 disclosed in WO 2009/139392 A1.

Using prpoH_01_RhDmpA(3) as a template plasmid, a gene sequence was designed in order to site-specifically introduce an amino acid mutation into the amino acid sequence of RhDmpA3 (purchased from GenScript Japan Inc.).

Using the generated expression plasmid as a template DNA, a DNA fragment of about 1.2 kb was amplified by PCR using a primer (DmpA3-Fw.) and a primer (DmpA3-Rv.) for the gene sequence encoding mutant RhDmpA3. For PCR, PrimeSTAR Max DNA Polymerase (Takara Bio Inc.) was used, and 1 cycle (98° C., 1 min), 25 cycles (98° C., 10 sec, 55° C., 62 sec, 72° C., 18 sec), 1 cycle (72° C., 5 min), and 1 cycle (4° C., hold) were set with the reaction solution composition described in the instruction manual. Using an expression vector pET-28a(+) (purchased from Merck) as a template DNA, a primer (pET28a-Fw.) and a primer (pET28a-Rv.) were used to obtain a DNA fragment of about 5.3 kb. For PCR, PrimeSTAR Max DNA Polymerase (Takara Bio Inc.) was used, and 1 cycle (98° C., 1 min), 25 cycles (98° C., 10 sec, 62° C., 5 sec, 72° C., 80 sec), 1 cycle (72° C., 5 min), and 1 cycle (4° C., hold) were set with the reaction solution composition described in the instruction manual. The obtained DNA fragment of about 1.2 kb and DNA fragment of about 5.3 kb were ligated with In-Fusion HD Cloning Kit (purchased from Takara Bio Inc.), *E. coli* JM109 was transformed with the obtained reaction solution, and a target plasmid was extracted from kanamycin-resistant strains. The mutant number and the introduced mutation points are as follows.

TABLE 1

Primers used to generate histidine-tagged mutant RhDmpA3 expression plasmid

| Name | Sequence |
|---|---|
| pET28a-Rv. | 5'-ATGGCTGCCGCGCGGCACCA GGCCGCTGCTGT-3' (SEQ ID NO: 3) |
| pET28a-Fw. | 5'-CTCGAGCACCACCACCACCA CCACTGAGAT-3' (SEQ ID NO: 4) |

TABLE 1-continued

Primers used to generate histidine-tagged mutant RhDmpA3 expression plasmid

| Name | Sequence |
|---|---|
| DmpA3-Fw. | 5'-CCGCGCGGCAGCCATATGGA ACGTAAACGCATTCGCGAACTGC TCCCGAATTT-3' (SEQ ID NO: 5) |
| DmpA3-Rv. | 5'-GTGGTGGTGCTCGAGTTAAT AGGCATGGCGGGTAACAATTTCTT TGAGTTTCT-3' (SEQ ID NO: 6) |

TABLE 2

Introduced mutation points of histidine-tagged mutant RhDmpA3

| No. | Mutation point to be introduced |
|---|---|
| 1 | I136V |
| 2 | F140A |
| 3 | F140Y |
| 4 | G142A |
| 5 | W143F |
| 6 | W143A |
| 7 | I147A |
| 8 | Q219A |
| 9 | T229A |
| 10 | P255A |
| 11 | E256A |
| 12 | E256D |
| 13 | I260A |
| 14 | Y295A |
| 15 | Y295W |
| 16 | I299V |
| 17 | I299F |
| 18 | F140H |
| 19 | F140W |
| 20 | F140Q |
| 21 | F140D |
| 22 | F140Y/Y295A |
| 23 | F140Y/Y295W |
| 24 | F140Y/Y295V |

Example 3: Purification of Histidine-Tagged RhDmpA3

(1) Generation of Enzyme-Producing Strain

*E. coli* BL21 (DE3) was transformed by a plasmid expressing RhDmpA3 (wild-type enzyme) to which a histidine tag was added and a mutant enzyme, and an expression strain having the plasmid was obtained from kanamycin-resistant strains.

(2) Preparation of Cell-Free Extract

The expression strain generated in (1) was inoculated into 3 mL of an LB medium containing 50 mg/L kanamycin, and shake-cultured at 33° C. using a test tube, and seed culture was performed by a culture time of 16 hours. 0.1 mL of the seed culture medium was inoculated into 20 mL of Overnight Express™ Instant TB Medium (Novagen) containing 50 mg/L kanamycin in a Sakaguchi flask, and shake-cultured at 25° C. to prepare a culture solution in 24 hours. Using 10 mL of the culture medium as a starting material, bacteria were collected by centrifugation (12,000×g, 5 minutes, 4° C.), resuspended with 2 mL of xTractor buffer (Takara Bio Inc.), and allowed to stand at room temperature for 20 minutes to obtain a microbial cell disrupted liquid. The obtained microbial cell disrupted liquid was centrifuged (15,000×g, 20 minutes, 4° C.) to separate insoluble fractions. The resulting supernatant was obtained as a cell-free extract. The cell-free extract was heated for 1 hour using a water bath at 55° C. After the heat treatment, the cell-free extract was rapidly cooled in an ice bath, the insoluble matter was separated by centrifugation (15,000×g, 10 minutes, 4° C.), and the supernatant was collected to obtain a crude purified enzyme solution.

(3) Affinity Chromatography

Using the cell-free extract as a starting material, an affinity enzyme was performed by TALON (registered trademark) Spin Column (Takara Bio Inc.) according to a manufacturer protocol. Equilibration Buffer contained in HisTALON Buffer set (Takara Bio Inc.) was used as an equilibration buffer, and Elution buffer contained in HisTALON Buffer set (Takara Bio Inc.) was used as an elution buffer. The obtained eluate was collected, and buffer exchange was performed with Amicon ultra 0.5 10 kda (Merck) into 50 mmol/L Tris-HCl buffer (pH 7.6) to obtain a purified enzyme solution.

Example 4: Measurement of Carnosine Production Activity of Histidine-Tagged RhDmpA3

Carnosine production activity was measured under the following conditions using β-Ala-OMe and L-His as substrates. A composition of 100 mM borate buffer, 100 mM KCl, 50 mM β-Ala-OMe, 100 mM L-His, enzyme solution, and pH 8.5 was prepared, a reaction was performed at 25° C., and the reaction was stopped by 50 mM $NaH_2PO_4$ (adjusted to pH 2.5 with phosphoric acid) after 15 minutes. The reaction stop solution was subjected to HPLC analysis to quantify the produced carnosine.

HPLC analysis conditions are as follows.

Analysis Condition 1:

Column: Capsule Pack UG type UG80S5 type UG80, functional group SCX, particle size 5 micron, inner diameter 2 mm, length 150 mm (OSAKA SODA CO., LTD.)

Mobile phase: 50 mmol/L $NaH_2PO_4$ (adjusted to pH 2.5 by phosphoric acid)

Flow rate: 1.0 mL/min

Column temperature: 40° C.

Detection: UV 210 nm

Under these conditions, an amount of enzyme capable of producing 1 μmol of carnosine per minute was defined as 1 U.

The protein concentration of the enzyme solution was quantified according to the method described in the instruction manual of Protein Assay CBB Solution (5× concentrate) (NACALAI TESQUE, INC.). Regarding a standard protein, Quick Start Bovine Serum Albumin Standard (Bio-Rad Laboratories, Inc.) was used to prepare a calibration curve, and the protein concentration in the sample was calculated.

Enzyme activity was measured using the purified preparations of RhDmpA3 (wild-type enzyme) and a mutant enzyme prepared in Example 3, and activity values per unit protein weight were compared.

TABLE 3

Enzyme activity of RhDmpA3 mutant

| Introduced mutation | Carnosine production activity (U/mg) |
|---|---|
| Wild type | 34.1 |
| I136V | 35.5 |
| F140Y | 42.3 |
| W143A | 34.6 |
| I260A | 37.7 |
| Y295A | 99.5 |
| Y295W | 48.2 |
| F140W | 67.0 |
| F140Q | 36.7 |
| F140Y/Y295A | 77.6 |
| F140Y/Y295W | 63.9 |
| F140Y/Y295V | 34.8 |

Example 5: Measurement of Carnosine Synthesis Yield by Histidine-Tagged RhDmpA3

Carnosine synthesis reaction using β-Ala-OMe and L-His as substrates was performed using the purified preparations of RhDmpA3 (wild-type enzyme) and a mutant enzyme prepared in Example 3. A reaction was performed at 25° C. for 2 hours with a composition of 100 mM borate buffer, 100 mM β-Ala-OMe, 100 mM L-His, and 1 U/0.2 mL of purified enzyme.

TABLE 4

Carnosine yield by RhDmpA3 mutant

| Introduced mutation | Carnosine synthesis yield (mol % based on β-Ala-Ome) |
|---|---|
| Wild type | 51.5 |
| I136V | 55.9 |
| F140A | 66.3 |
| F140Y | 58.7 |
| W143F | 57.9 |
| W143A | 60.7 |
| I147A | 54.4 |
| Q219A | 56.3 |
| T229A | 52.0 |
| P255A | 63.6 |
| E256A | 52.5 |
| I260A | 59.8 |
| Y295A | 59.1 |
| Y295W | 55.8 |
| I299V | 62.7 |
| I299F | 60.0 |
| F140H | 66.2 |
| F140W | 57.2 |
| F140Q | 53.9 |
| F140D | 53.3 |
| F140Y/Y295A | 57.9 |
| F140Y/Y295V | 52.1 |

Example 6: Thermal Stability Measurement of Histidine-Tagged RhDmpA3

Enzyme activity was measured after heating the purified preparations of RhDmpA3 (wild-type enzyme) and a mutant enzyme prepared in Example 3, and thermal stability was measured by comparing activity values per unit protein weight before and after the heat treatment.

Heating of the purified preparations of RhDmpA3 (wild-type enzyme) and a mutant enzyme was performed under the following conditions. The purified enzyme solution prepared in Example 3 was heated at 60° C. for 2 hours and stored on ice until measurement of enzyme activity.

Carnosine production activity was measured under the following conditions using β-Ala-OMe and L-His as substrates. A composition of 100 mM borate buffer, 100 mM KCl, 50 mM β-Ala-OMe, 100 mM L-His, and enzymatic solution, and pH 8.5 was prepared, a reaction was performed at 25° C., and the reaction was stopped by 50 mM $NaH_2PO_4$ (adjusted to pH 2.5 with phosphoric acid) after 15 minutes. The reaction stop solution was subjected to HPLC analysis to quantify the produced carnosine.

Under these conditions, a ratio of the residual enzyme activity of the enzyme solution after heating to the enzyme activity of the enzyme solution before heating was calculated and defined as the thermal stability of the enzyme.

TABLE 5

Thermal stability of RhDmpA3 mutant

| Introduced mutation | Residual activity (%) |
|---|---|
| Wild type | 23.6 |
| I136V | 91.4 |
| T139S | 75.3 |
| T139A | 62.4 |
| F140Y | 49.4 |
| W143F | 64.2 |
| E256A | 65.4 |
| E256D | 64.8 |
| I299F | 86.4 |
| F140W | 83.2 |
| F140N | 48.3 |

Example 7: Measurement of Anserine Production Activity of Histidine-Tagged RhDmpA3

Enzyme activity was measured using the purified preparations of RhDmpA3 (wild-type enzyme) and a mutant enzyme prepared in Example 3, and activity values per unit protein weight were compared.

Anserine production activity was measured under the following conditions using β-Ala-OMe and 3-Methyl-L-His as substrates. A composition of 100 mM borate buffer, 100 mM KCl, 50 mM β-Ala-OMe, 100 mM 3-Methyl-L-His, enzyme solution, and pH 8.5 was prepared, a reaction was performed at 25° C., and the reaction was stopped by 50 mM $NaH_2PO_4$ (adjusted to pH 2.5 with phosphoric acid) after 15 minutes. The reaction stop solution was subjected to HPLC analysis to quantify the produced anserine.

HPLC analysis conditions are as follows.

Analysis Condition 1:

- Column: Capsule Pack UG type UG80S5 type UG80, functional group SCX, particle size 5 micron, inner diameter 2 mm, length 150 mm (OSAKA SODA CO., LTD.)
- Mobile phase: 50 mmol/L $NaH_2PO_4$ (adjusted to pH 2.5 by phosphoric acid)
- Flow rate: 1.0 mL/min
- Column temperature: 40° C.
- Detection: UV 210 nm Under these conditions, an amount of enzyme capable of producing 1 μmol of anserine per minute was defined as 1 U.

The protein concentration of the enzyme solution was quantified according to the method described in the instruction manual of Protein Assay CBB Solution (5× concentrate) (NACALAI TESQUE, INC.). Regarding a standard protein, Quick Start Bovine Serum Albumin Standard (Bio-Rad Laboratories, Inc.) was used to prepare a calibration curve, and the protein concentration in the sample was calculated.

Enzyme activity was measured using the purified preparations of RhDmpA3 (wild-type enzyme) and a mutant enzyme prepared in Example 3, and activity values per unit protein weight were compared.

TABLE 6

Enzyme activity of RhDmpA3 mutant

| Introduced mutation | Anserine production activity (U/mg) |
|---|---|
| Wild type | 75.3 |
| I136V | 75.8 |
| G142A | 99.1 |
| W143F | 77.1 |
| W143A | 75.3 |
| T229A | 86.8 |
| E256D | 80.1 |
| Y295A | 93.6 |
| F140Y/Y295A | 91.8 |

Example 8: Measurement of Anserine Synthesis Yield by Histidine-Tagged RhDmpA3

Anserine synthesis reaction using β-Ala-OMe and 3-Methyl-L-His as substrates was performed using the purified preparations of RhDmpA3 (wild-type enzyme) and a mutant enzyme prepared in Example 3. A reaction was performed at 25° C. for 2 hours with a composition of 100 mM borate buffer, 100 mM β-Ala-OMe, 100 mM 3-Methyl-L-His, and 1 U/0.2 mL of purified enzyme.

TABLE 7

Anserine yield by RhDmpA3 mutant

| Introduced mutation | Anserine synthesis yield (mol % based on β-Ala-Ome) |
|---|---|
| Wild type | 72.4 |
| F140A | 77.7 |
| F140Y | 76.1 |
| G142A | 79.3 |
| W143F | 76.0 |
| W143A | 79.5 |
| P255A | 72.7 |
| Y295A | 73.7 |
| I299V | 74.7 |
| I299F | 77.3 |
| F140H | 87.0 |
| F140W | 76.7 |
| F140Y/Y295A | 73.8 |
| F140Y/Y295W | 73.2 |
| F140Y/Y295V | 73.0 |

Example 9: Generation of Further Mutant

In addition to the mutants described above, the following mutants were further generated. In order to site-specifically introduce an amino acid mutation into the amino acid sequence of RhDmpA3 using the above plasmid prpoH_01_RhDmpA(3) as a template plasmid, a DNA fragment of about 3.8 kb was amplified by PCR using a primer (Fw.) and a primer (Rv.). For PCR, PrimeSTAR Max DNA Polymerase (Takara Bio Inc.) was used, and 1 cycle (98° C., 1 min), 25 cycles (98° C., 10 sec, 55° C., 62 sec, 72° C., 18 sec), 1 cycle (72° C., 5 min), and 1 cycle (4° C., hold) were set with the reaction solution composition described in the instruction manual. *E. coli* JM109 was transformed with a reaction solution obtained by treating the obtained reaction solution with DpnI, and a target plasmid was extracted from ampicillin-resistant strains. The introduced mutation points and primer sequences are as follows.

TABLE 8

Introduced mutation points of further mutants and primers used for plasmid generation

| Introduced mutation | Template* | Primer |
|---|---|---|
| I201F | WT | Forward: GTTAAAtttGACAGCAAAGGCGAGAAA (SEQ ID NO: 7)<br>Reverse: GCTGTCaaaTTTAACGGAATCGATCAC (SEQ ID NO: 8) |
| A249F | WT | Forward: AAGAAAtttGGCCCAATGGATGGGCCG (SEQ ID NO: 9)<br>Reverse: TGGGCCaaaTTTCTTCGCCGCCATTGC (SEQ ID NO: 10) |
| A249L | WT | Forward: AAGAAAttgGGCCCAATGGATGGGCCG (SEQ ID NO: 11)<br>Reverse: TGGGCCcaaTTTCTTCGCCGCCATTGC (SEQ ID NO: 12) |
| S293F | WT | Forward: TGGGGTtttAACTACTCTGGCGACATC (SEQ ID NO: 13)<br>Reverse: GTAGTTaaaACCCCAGCCACCTGTACG (SEQ ID NO: 14) |
| I181V | WT | Forward: GGAATGgttACCATGGGCTTCAAAGCT (SEQ ID NO: 15)<br>Reverse: CATGGTaacCATTCCGGTACCTCCGCC (SEQ ID NO: 16) |
| I127V | WT | Forward: AAAGGAgttTGCGACTGGTTCCTGACT (SEQ ID NO: 17)<br>Reverse: GTCGCAaacTCCTTTCTCATCCTTGTG (SEQ ID NO: 18) |

TABLE 8-continued

Introduced mutation points of further mutants and primers used for plasmid generation

| Introduced mutation | Template* | Primer |
|---|---|---|
| N294H | WT | Forward: GGTTCGcatTACTCTGGCGACATCTTT (SEQ ID NO: 19)<br>Reverse: AGAGTAatgCGAACCCCAGCCACCTGT (SEQ ID NO: 20) |
| E81D | WT | Forward: TCTGGCgatATGACCGGCTCCCATTGG (SEQ ID NO: 21)<br>Reverse: GGTCATatcGCCAGAGCCGTTGAACCG (SEQ ID NO: 22) |
| M244L | WT | Forward: GAAGCAttgGCGGCGAAGAAAGCAGGC (SEQ ID NO: 23)<br>Reverse: CGCCGCcaaTGCTTCATCTTCGAGAAT (SEQ ID NO: 24) |
| I127L | WT | Forward: AAAGGAttgTGCGACTGGTTCCTGACT (SEQ ID NO: 25)<br>Reverse: GTCGCAcaaTCCTTTCTCATCCTTGTG (SEQ ID NO: 26) |

*The plasmid used as the template is the WT described above.

Using the generated expression plasmid as a template DNA, a DNA fragment of about 1.2 kb was amplified by PCR using a primer (DmpA3-Fw.) and a primer (DmpA3-Rv.) for the gene sequence encoding mutant RhDmpA3. For PCR, PrimeSTAR Max DNA Polymerase (Takara Bio Inc.) was used, and 1 cycle (98° C., 1 min), 25 cycles (98° C., 10 sec, 55° C., 62 sec, 72° C., 18 sec), 1 cycle (72° C., 5 min), and 1 cycle (4° C., hold) were set with the reaction solution composition described in the instruction manual. Using an expression vector pET-28a(+) (purchased from Merck) as a template DNA, a primer (pET28a-Fw.) and a primer (pET28a-Rv.) were used to obtain a DNA fragment of about 5.3 kb. For PCR, PrimeSTAR Max DNA Polymerase (Takara Bio Inc.) was used, and 1 cycle (98° C., 1 min), 25 cycles (98° C., 10 sec, 62° C., 5 sec, 72° C., 80 sec), 1 cycle (72° C., 5 min), and 1 cycle (4° C., hold) were set with the reaction solution composition described in the instruction manual. The obtained DNA fragment of about 1.2 kb and DNA fragment of about 5.3 kb were ligated with In-Fusion HD Cloning Kit (purchased from Takara Bio Inc.), *E. coli* JM109 was transformed with the obtained reaction solution, and a target plasmid was extracted from kanamycin-resistant strains.

TABLE 9

| Primers used to generate histidine-tagged mutant RhDmpA3 expression plasmid | |
|---|---|
| Name | Sequence |
| pET28a-Rv. | 5'-ATGGCTGCCGCGCGGCACCAGGCCGCTGCTGT-3' (SEQ ID NO: 3) |
| pET28a-Fw. | 5'-CTCGAGCACCACCACCACCACCACTGAGAT-3' (SEQ ID NO: 4) |
| DmpA3-Fw. | 5'-CCGCGCGGCAGCCATATGGAACGTAAACGCATTC GCGAACTGCTCCCGAATTT-3' (SEQ ID NO: 5) |
| DmpA3-Rv. | 5'-GTGGTGGTGCTCGAGTTAATAGGCATGGCGGG TAACAATTTCTTTGAGTTTCT-3' (SEQ ID NO: 6) |

Example 10: Purification of Further Histidine-Tagged RhDmpA3

(1) Generation of Enzyme-Producing Strain

*E. coli* BL21 (DE3) was transformed by a plasmid expressing RhDmpA3 (wild-type enzyme) to which a histidine tag was added and a mutant enzyme, and an expression strain having the plasmid was obtained from kanamycin-resistant strains.

(2) Preparation of Cell-Free Extract

The expression strain generated in (1) was inoculated into 3 mL of an LB medium containing 50 mg/L kanamycin, and shake-cultured at 33° C. using a test tube, and seed culture was performed by a culture time of 16 hours. 0.1 mL of the seed culture medium was inoculated into 20 mL of Overnight Express™ Instant TB Medium (Novagen) containing 50 mg/L kanamycin in a Sakaguchi flask, and shake-cultured at 25° C. to prepare a culture solution in 24 hours. Using 10 mL of the culture medium as a starting material, bacteria were collected by centrifugation (12,000×g, 5 minutes, 4° C.), resuspended with 2 mL of xTractor buffer (Takara Bio Inc.), and allowed to stand at room temperature for 20 minutes to obtain a microbial cell disrupted liquid. The obtained microbial cell disrupted liquid was centrifuged (15,000×g, 20 minutes, 4° C.) to separate insoluble fractions. The resulting supernatant was obtained as a cell-free extract. The cell-free extract was heated for 1 hour using a water bath at 55° C. After the heat treatment, the cell-free extract was rapidly cooled in an ice bath, the insoluble matter was separated by centrifugation (15,000×g, 10 minutes, 4° C.), and the supernatant was collected to obtain a crude purified enzyme solution.

(3) Affinity Chromatography

Using the cell-free extract as a starting material, an affinity enzyme was performed by TALON (registered trademark) Spin Column (Takara Bio Inc.) according to a manufacturer protocol. Equilibration Buffer contained in HisTALON Buffer set (Takara Bio Inc.) was used as an equilibration buffer, and Elution buffer contained in HisTALON Buffer set (Takara Bio Inc.) was used as an elution buffer. The obtained eluate was collected, and buffer exchange was performed with Amicon ultra 0.5 10 kda (Merck) into 50 mmol/L Tris-HCl buffer (pH 7.6) to obtain a purified enzyme solution.

Example 11: Measurement of Carnosine Production Activity of Histidine-Tagged RhDmpA3

Carnosine production activity was measured under the following conditions using β-Ala-OMe and L-His as substrates. A composition of 100 mM borate buffer, 100 mM KCl, 50 mM β-Ala-OMe, 100 mM L-His, enzyme solution, and pH 8.5 was prepared, a reaction was performed at 25° C., and the reaction was stopped by 50 mM $NaH_2PO_4$ (adjusted to pH 2.5 with phosphoric acid) after 15 minutes. The reaction stop solution was subjected to HPLC analysis to quantify the produced carnosine.

HPLC analysis conditions are as follows.

Analysis Condition 1:

Column: Capsule Pack UG type UG80S5 type UG80, functional group SCX, particle size 5 micron, inner diameter 2 mm, length 150 mm (OSAKA SODA CO., LTD.) Mobile phase: 50 mmol/L $NaH_2PO_4$ (adjusted to pH 2.5 by phosphoric acid)

Flow rate: 1.0 mL/min

Column temperature: 40° C.

Detection: UV 210 nm

Under these conditions, an amount of enzyme capable of producing 1 μmol of carnosine per minute was defined as 1 U.

The protein concentration of the enzyme solution was quantified according to the method described in the instruction manual of Protein Assay CBB Solution (5× concentrate) (NACALAI TESQUE, INC.). Regarding a standard protein, Quick Start Bovine Serum Albumin Standard (Bio-Rad Laboratories, Inc.) was used to prepare a calibration curve, and the protein concentration in the sample was calculated.

Enzyme activity was measured using the purified preparations of RhDmpA3 (wild-type enzyme) and a mutant enzyme prepared in Example 10, and activity values per unit protein weight were compared.

TABLE 10

Enzyme activity of RhDmpA3 mutant

| Introduced mutation | Carnosine production activity (U/mg) |
|---|---|
| Wild type | 34.1 |
| S293F | 58.0 |
| I127V | 36.6 |

Example 12: Measurement of Carnosine Synthesis Yield by Histidine-Tagged RhDmpA3

Carnosine synthesis reaction using β-Ala-OMe and L-His as substrates was performed using the purified preparations of RhDmpA3 (wild-type enzyme) and a mutant enzyme prepared in Example 10. A reaction was performed at 25° C. for 2 hours with a composition of 100 mM borate buffer, 100 mM β-Ala-OMe, 100 mM L-His, and 1 U/0.2 mL of purified enzyme.

TABLE 11

Carnosine yield by RhDmpA3 mutant

| Introduced mutation | Carnosine synthesis yield (mol % based on β-Ala-Ome) |
|---|---|
| Wild type | 51.5 |
| I201F | 57.0 |
| A249L | 57.6 |
| I181V | 60.5 |
| I127V | 60.7 |

TABLE 11-continued

| Carnosine yield by RhDmpA3 mutant | |
|---|---|
| Introduced mutation | Carnosine synthesis yield (mol % based on β-Ala-Ome) |
| N294H | 57.7 |
| E81D | 58.3 |
| M244L | 57.2 |
| I127L | 58.0 |

Example 13: Measurement of Anserine Production Activity of Histidine-Tagged RhDmpA3

Enzyme activity was measured using the purified preparations of RhDmpA3 (wild-type enzyme) and a mutant enzyme prepared in Example 10, and activity values per unit protein weight were compared.

Anserine production activity was measured under the following conditions using β-Ala-OMe and 3-Methyl-L-His as substrates. A composition of 100 mM borate buffer, 100 mM KCl, 50 mM β-Ala-OMe, 100 mM 3-Methyl-L-His, enzyme solution, and pH 8.5 was prepared, a reaction was performed at 25° C., and the reaction was stopped by 50 mM $NaH_2PO_4$ (adjusted to pH 2.5 with phosphoric acid) after 15 minutes. The reaction stop solution was subjected to HPLC analysis to quantify the produced anserine.

HPLC analysis conditions are as follows.

Analysis Condition 1:

- Column: Capsule Pack UG type UG80S5 type UG80, functional group SCX, particle size 5 micron, inner diameter 2 mm, length 150 mm (OSAKA SODA CO., LTD.)
- Mobile phase: 50 mmol/L $NaH_2PO_4$ (adjusted to pH 2.5 by phosphoric acid)
- Flow rate: 1.0 mL/min
- Column temperature: 40° C.
- Detection: UV 210 nm Under these conditions, an amount of enzyme capable of producing 1 μmol of anserine per minute was defined as 1 U.

The protein concentration of the enzyme solution was quantified according to the method described in the instruction manual of Protein Assay CBB Solution (5× concentrate) (NACALAI TESQUE, INC.). Regarding a standard protein, Quick Start Bovine Serum Albumin Standard (Bio-Rad Laboratories, Inc.) was used to prepare a calibration curve, and the protein concentration in the sample was calculated.

Enzyme activity was measured using the purified preparations of RhDmpA3 (wild-type enzyme) and a mutant enzyme prepared in Example 10, and activity values per unit protein weight were compared.

TABLE 12

| Enzyme activity of RhDmpA3 mutant | |
|---|---|
| Introduced mutation | Anserine production activity (U/mg) |
| Wild type | 75.3 |
| A249F | 78.4 |
| S293F | 76.1 |
| I127V | 77.8 |

Example 14: Measurement of Anserine Synthesis Yield by Histidine-Tagged RhDmpA3

Anserine synthesis reaction using β-Ala-OMe and 3-Methyl-L-His as substrates was performed using the purified preparations of RhDmpA3 (wild-type enzyme) and a mutant enzyme prepared in Example 10. A reaction was performed at 25° C. for 2 hours with a composition of 100 mM borate buffer, 100 mM β-Ala-OMe, 100 mM 3-Methyl-L-His, and 1 U/0.2 mL of purified enzyme.

TABLE 13

| Anserine yield by RhDmpA3 mutant | |
|---|---|
| Introduced mutation | Anserine synthesis yield (mol % based on β-Ala-Ome) |
| Wild type | 72.4 |
| I201F | 73.4 |
| A249L | 75.0 |
| I181V | 72.8 |
| I127V | 75.8 |
| N294H | 76.4 |
| E81D | 73.4 |
| M244L | 74.0 |
| I127L | 76.8 |

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A modified enzyme comprising:

(A) an amino acid sequence of SEQ ID NO. 1, wherein the amino acid sequence additionally comprises a mutation of an amino acid residue selected from the group consisting of E81, I127, I136, T139, F140, G142, W143, I147, I181, I201, Q219, T229, M244, A249, P255, E256, I260, S293, N294, Y295, I299, and combinations thereof;

(B) the amino acid sequence of (A) comprising an additional mutation of substitution, deletion, insertion, and addition of one or more amino acid residues; or (C) an amino acid sequence having 90% or more identity to said amino acid sequence of (A) or (B); and wherein an imidazole dipeptide production activity or thermal stability is enhanced in the modified enzyme relative to an enzyme of the amino acid sequence of SEQ ID NO: 1.

2. The modified enzyme according to claim 1, wherein the mutation of (A) is:

(1) E81D;
(2) I127V or I127L;
(3) I136V;
(4) T139S or T139A;
(5) F140A, F140Y, F140H, F140W, F140Q, F140N, or F140D;
(6) G142A;
(7) W143F or W143A;
(8) I147A;
(9) I181V;
(10) I201F;
(11) Q219A;
(12) T229A;
(13) M244L;
(14) A249F or A249L;
(15) P255A;
(16) E256A or E256D;
(17) I260A;
(18) S293F;
(19) N294H;
(20) Y295A, Y295W, or Y295V; or
(21) I299V or I299F.

3. The modified enzyme according to claim 1, wherein the imidazole dipeptide production activity is an activity of producing an imidazole dipeptide from an amino acid ester and an L-amino acid having an imidazole group in a side chain.

4. The modified enzyme according to claim 3, wherein the amino acid ester is a compound represented by the following formula (I):

(I)

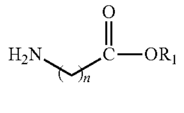

wherein $R_1$ is an alkyl group having 1 to 3 carbon atoms, and n is an integer of 1 to 4;

the L-amino acid having an imidazole group in a side chain is an L-form of a compound represented by the following formula (II):

(II)

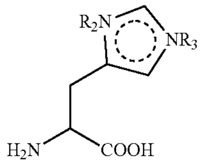

wherein $R_2$ and $R_3$ are each independently absent, a hydrogen atom, or an alkyl group having 1 to 3 carbon atoms; and the imidazole dipeptide is represented by the following formula (III):

(III)

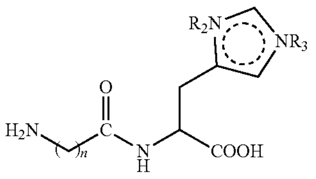

wherein $R_2$ and $R_3$ are the same as in said formula (II), and n is the same as in said formula (I).

5. The modified enzyme according to claim 3, wherein the imidazole dipeptide is carnosine or anserine.

6. A polynucleotide encoding the modified enzyme according to claim 1.

7. An expression vector comprising the polynucleotide according to claim 6.

8. A host cell comprising an expression unit containing a polynucleotide encoding the modified enzyme according to claim 1 and a promoter operably linked thereto.

9. A method of producing an imidazole dipeptide or a salt thereof, comprising contacting an amino acid ester or a salt thereof and an L-amino acid having an imidazole group in a side chain or a salt thereof with the modified enzyme according claim 1 to form the imidazole dipeptide or the salt thereof.

10. The method according to claim 9, wherein said contacting is performed using said modified enzyme.

11. The method according to claim 9, wherein said contacting is performed using a host cell comprising an expression unit containing a polynucleotide encoding the modified enzyme and a promoter operably linked thereto.

12. The method according to claim 9, wherein the amino acid ester is a compound represented by said formula (I), the L-amino acid having an imidazole group in a side chain is an L-form of a compound represented by said formula (II), and the imidazole dipeptide is represented by said formula (III).

13. The method according to claim 9, wherein the imidazole dipeptide is carnosine or anserine.

* * * * *

SEQUENCE LISTING

```
Sequence total quantity: 26
SEQ ID NO: 1            moltype = AA  length = 383
FEATURE                 Location/Qualifiers
source                  1..383
                        mol_type = protein
                        organism = Rhodotorula minuta
SEQUENCE: 1
MERKRIRELL PNLRFGQFPT GPKNSLTDVP GVLVSTKSVI KPADLPHHHE VNTGVTTILP  60
RKEWFKQGCY ASYFRFNGSG EMTGSHWIDE SGLLNSPVII TNSFGVGACY NGVYEYAKKH  120
HKDEKGICDW FLTPVIAETF DGWLSDIGAM AVQSSDVVEG IENASSDAVP EGCTGGGTGM  180
ITMGFKAGTG NASRVIDSVK IDSKGEKQQV KYTLAALVQS NFGGARFLTV NGVPVGRILE  240
DEAMAAKKAG PMDGPEGSII VVIATDAPLI PIQLQRLAKR ATVGVARTGG WGSNYSGDIF  300
LAFSTAHEIP RENTQNWTPS VPQPQEVLDT ESINALFEAA FEAVEEAIYN AICMATDTKG  360
PDGREVKAID LEKLKEIVTR HAY                                         383

SEQ ID NO: 2            moltype = DNA  length = 250
FEATURE                 Location/Qualifiers
```

-continued

```
source                  1..250
                        mol_type = other DNA
                        organism = Escherichia coli
SEQUENCE: 2
gaataataaa agcgtgttat actctttccc tgcaatgggt tccgtagcag ggaaagagac  60
cccgttgtct cttcccggta tttcatctct atgtcacatt ttgtgcgtaa tttattcaca  120
agcttgcatt gaacttgtgg ataaaatcac ggtctgataa aacagtgaat gataacctcg  180
ttgctcttaa gctctggcac agttgttgct accactgaag cgccagaaga tatcgattga  240
gaggatttga                                                         250

SEQ ID NO: 3            moltype = DNA  length = 32
FEATURE                 Location/Qualifiers
misc_feature            1..32
                        note = Primer
source                  1..32
                        mol_type = other DNA
                        organism = synthetic construct
SEQUENCE: 3
atggctgccg cgcggcacca ggccgctgct gt                                32

SEQ ID NO: 4            moltype = DNA  length = 30
FEATURE                 Location/Qualifiers
misc_feature            1..30
                        note = Primer
source                  1..30
                        mol_type = other DNA
                        organism = synthetic construct
SEQUENCE: 4
ctcgagcacc accaccacca ccactgagat                                   30

SEQ ID NO: 5            moltype = DNA  length = 53
FEATURE                 Location/Qualifiers
misc_feature            1..53
                        note = Primer
source                  1..53
                        mol_type = other DNA
                        organism = synthetic construct
SEQUENCE: 5
ccgcgcggca gccatatgga acgtaaacgc attcgcgaac tgctcccgaa ttt         53

SEQ ID NO: 6            moltype = DNA  length = 53
FEATURE                 Location/Qualifiers
misc_feature            1..53
                        note = Primer
source                  1..53
                        mol_type = other DNA
                        organism = synthetic construct
SEQUENCE: 6
gtggtggtgc tcgagttaat aggcatggcg ggtaacaatt tctttgagtt tct         53

SEQ ID NO: 7            moltype = DNA  length = 27
FEATURE                 Location/Qualifiers
misc_feature            1..27
                        note = Primer
source                  1..27
                        mol_type = other DNA
                        organism = synthetic construct
SEQUENCE: 7
gttaaatttg acagcaaagg cgagaaa                                      27

SEQ ID NO: 8            moltype = DNA  length = 27
FEATURE                 Location/Qualifiers
misc_feature            1..27
                        note = Primer
source                  1..27
                        mol_type = other DNA
                        organism = synthetic construct
SEQUENCE: 8
gctgtcaaat ttaacggaat cgatcac                                      27

SEQ ID NO: 9            moltype = DNA  length = 27
FEATURE                 Location/Qualifiers
misc_feature            1..27
                        note = Primer
source                  1..27
                        mol_type = other DNA
                        organism = synthetic construct
SEQUENCE: 9
aagaaatttg gcccaatgga tgggccg                                      27
```

-continued

```
SEQ ID NO: 10          moltype = DNA  length = 27
FEATURE                Location/Qualifiers
misc_feature           1..27
                       note = Primer
source                 1..27
                       mol_type = other DNA
                       organism = synthetic construct
SEQUENCE: 10
tgggccaaat ttcttcgccg ccattgc                                        27

SEQ ID NO: 11          moltype = DNA  length = 27
FEATURE                Location/Qualifiers
misc_feature           1..27
                       note = Primer
source                 1..27
                       mol_type = other DNA
                       organism = synthetic construct
SEQUENCE: 11
aagaaattgg gcccaatgga tgggccg                                        27

SEQ ID NO: 12          moltype = DNA  length = 27
FEATURE                Location/Qualifiers
misc_feature           1..27
                       note = Primer
source                 1..27
                       mol_type = other DNA
                       organism = synthetic construct
SEQUENCE: 12
tgggcccaat ttcttcgccg ccattgc                                        27

SEQ ID NO: 13          moltype = DNA  length = 27
FEATURE                Location/Qualifiers
misc_feature           1..27
                       note = Primer
source                 1..27
                       mol_type = other DNA
                       organism = synthetic construct
SEQUENCE: 13
tggggtttta actactctgg cgacatc                                        27

SEQ ID NO: 14          moltype = DNA  length = 27
FEATURE                Location/Qualifiers
misc_feature           1..27
                       note = Primer
source                 1..27
                       mol_type = other DNA
                       organism = synthetic construct
SEQUENCE: 14
gtagttaaaa ccccagccac ctgtacg                                        27

SEQ ID NO: 15          moltype = DNA  length = 27
FEATURE                Location/Qualifiers
misc_feature           1..27
                       note = Primer
source                 1..27
                       mol_type = other DNA
                       organism = synthetic construct
SEQUENCE: 15
ggaatggtta ccatgggctt caaagct                                        27

SEQ ID NO: 16          moltype = DNA  length = 27
FEATURE                Location/Qualifiers
misc_feature           1..27
                       note = Primer
source                 1..27
                       mol_type = other DNA
                       organism = synthetic construct
SEQUENCE: 16
catggtaacc attccggtac ctccgcc                                        27

SEQ ID NO: 17          moltype = DNA  length = 27
FEATURE                Location/Qualifiers
misc_feature           1..27
                       note = Primer
source                 1..27
                       mol_type = other DNA
                       organism = synthetic construct
SEQUENCE: 17
```

-continued

```
aaaggagttt gcgactggtt cctgact                                    27

SEQ ID NO: 18          moltype = DNA  length = 27
FEATURE                Location/Qualifiers
misc_feature           1..27
                       note = Primer
source                 1..27
                       mol_type = other DNA
                       organism = synthetic construct
SEQUENCE: 18
gtcgcaaact cctttctcat ccttgtg                                    27

SEQ ID NO: 19          moltype = DNA  length = 27
FEATURE                Location/Qualifiers
misc_feature           1..27
                       note = Primer
source                 1..27
                       mol_type = other DNA
                       organism = synthetic construct
SEQUENCE: 19
ggttcgcatt actctggcga catcttt                                    27

SEQ ID NO: 20          moltype = DNA  length = 27
FEATURE                Location/Qualifiers
misc_feature           1..27
                       note = Primer
source                 1..27
                       mol_type = other DNA
                       organism = synthetic construct
SEQUENCE: 20
agagtaatgc gaaccccagc cacctgt                                    27

SEQ ID NO: 21          moltype = DNA  length = 27
FEATURE                Location/Qualifiers
misc_feature           1..27
                       note = Primer
source                 1..27
                       mol_type = other DNA
                       organism = synthetic construct
SEQUENCE: 21
tctggcgata tgaccggctc ccattgg                                    27

SEQ ID NO: 22          moltype = DNA  length = 27
FEATURE                Location/Qualifiers
misc_feature           1..27
                       note = Primer
source                 1..27
                       mol_type = other DNA
                       organism = synthetic construct
SEQUENCE: 22
ggtcatatcg ccagagccgt tgaaccg                                    27

SEQ ID NO: 23          moltype = DNA  length = 27
FEATURE                Location/Qualifiers
misc_feature           1..27
                       note = Primer
source                 1..27
                       mol_type = other DNA
                       organism = synthetic construct
SEQUENCE: 23
gaagcattgg cggcgaagaa agcaggc                                    27

SEQ ID NO: 24          moltype = DNA  length = 27
FEATURE                Location/Qualifiers
misc_feature           1..27
                       note = Primer
source                 1..27
                       mol_type = other DNA
                       organism = synthetic construct
SEQUENCE: 24
cgccgccaat gcttcatctt cgagaat                                    27

SEQ ID NO: 25          moltype = DNA  length = 27
FEATURE                Location/Qualifiers
misc_feature           1..27
                       note = Primer
source                 1..27
                       mol_type = other DNA
                       organism = synthetic construct
```

-continued

```
SEQUENCE: 25
aaaggattgt gcgactggtt cctgact                                27

SEQ ID NO: 26          moltype = DNA  length = 27
FEATURE                Location/Qualifiers
misc_feature           1..27
                       note = Primer
source                 1..27
                       mol_type = other DNA
                       organism = synthetic construct
SEQUENCE: 26
gtcgcacaat cctttctcat ccttgtg                                27
```